United States Patent [19]

Mencacci et al.

[11] 4,003,302
[45] Jan. 18, 1977

[54] RETORT SYSTEM

[75] Inventors: Samuel A. Mencacci, San Jose; Jurgen H. Strasser, Mountain View; Tom Mansfield, San Jose, all of Calif.

[73] Assignee: FMC Corporation, San Jose, Calif.

[22] Filed: Nov. 8, 1974

[21] Appl. No.: 522,067

[52] U.S. Cl. .................................. 99/359; 426/232
[51] Int. Cl.² .......................................... A23L 3/02
[58] Field of Search ............ 99/359, 360, 366, 371, 99/403–404, 409, 467, 470, 370; 426/405, 407, 412, 232; 128/220; 137/206; 220/10; 285/24

[56] References Cited

UNITED STATES PATENTS

| 1,636,768 | 7/1927 | Ford | 99/359 UX |
| 2,374,425 | 4/1945 | De Weerth | 99/360 X |
| 2,472,970 | 6/1949 | Hanna | 99/370 |
| 2,629,312 | 2/1953 | Davis | 99/371 |
| 3,093,449 | 6/1963 | Kotarski et al. | 99/359 X |
| 3,215,538 | 11/1965 | Sada | 99/359 X |
| 3,365,311 | 1/1968 | Schmidt | 426/405 |
| 3,480,451 | 11/1969 | Hardison | 99/359 |
| 3,511,169 | 5/1970 | Fritzberg et al. | 99/370 |
| 3,531,300 | 9/1970 | Greenberg et al. | 426/232 |
| 3,733,202 | 5/1973 | Marmor | 99/404 X |
| 3,744,402 | 7/1973 | Piegza et al. | 99/360 |
| 3,769,028 | 10/1973 | Katz et al. | 426/232 |
| 3,776,257 | 12/1973 | Piegza | 220/10 X |

Primary Examiner—Leonard D. Christian
Assistant Examiner—Arthur O. Henderson
Attorney, Agent, or Firm—R. S. Kelly; A. J. Moore; C. E. Tripp

[57] ABSTRACT

A retort system for thin walled, generally flat containers filled with a food product or the like including a pressure vessel having one or more batches of flat containers therein disposed within a heat treatment tunnel. A heat transfer liquid is circulated through the tunnel parallel to the flat sidewalls of the containers at a rate sufficient to transfer heat between the fluid and the containers without incurring a large change in temperature of the liquid between the inlet and outlet of the tunnel for assuring uniform cooking of the contents of the containers. During a cooking cycle the liquid is reheated while being returned externally of the tunnel from the discharge end of the tunnel to the inlet end of the tunnel. The tunnel is partially defined by the side walls of nesting containers supporting trays, which trays may be rotated for an agitating cook or may be stationary for a still cook. In one embodiment of an agitating type retort system, carts are provided having reels thereon which are loaded and unloaded when in a vertical position and which are arranged to be disposed horizontally during processing to define a rotating radially extending tunnel within the pressure vessel.

24 Claims, 22 Drawing Figures

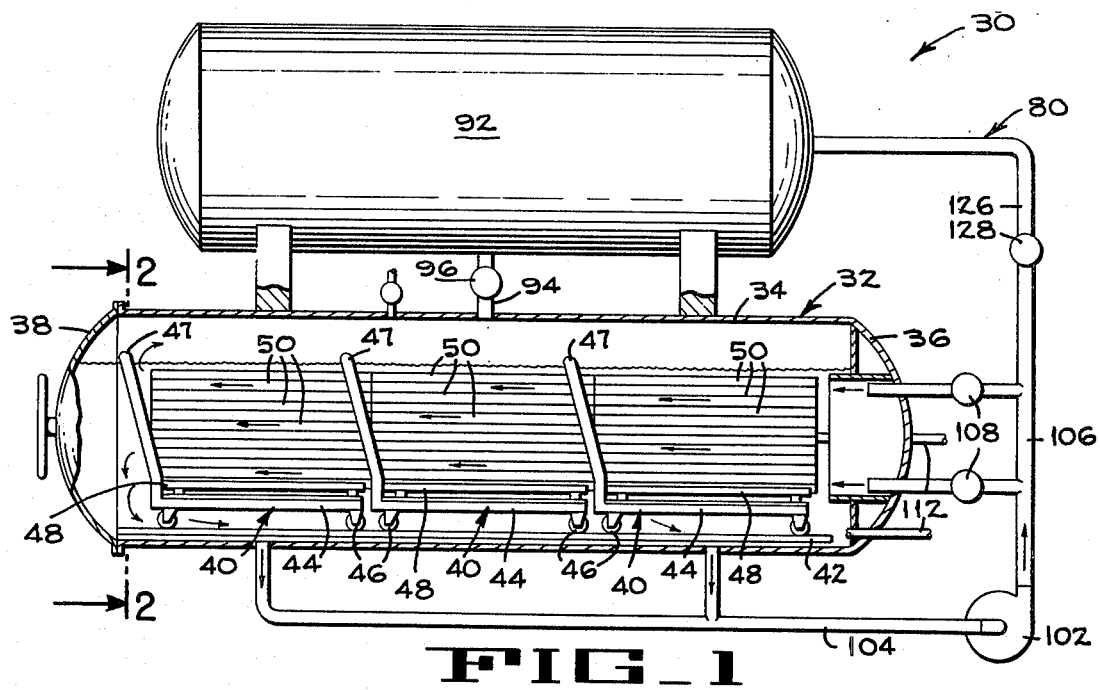
FIG_1
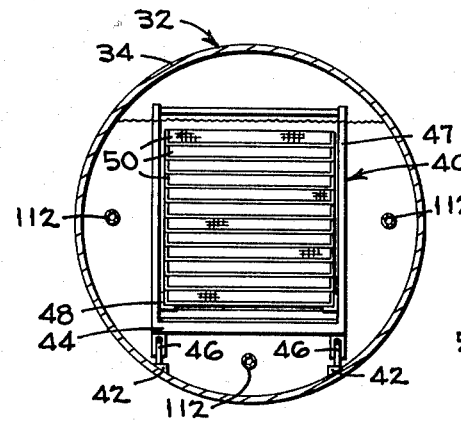
FIG_2
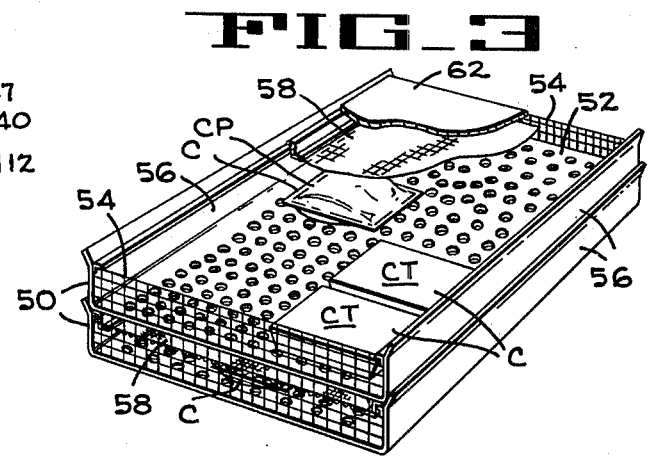
FIG_3
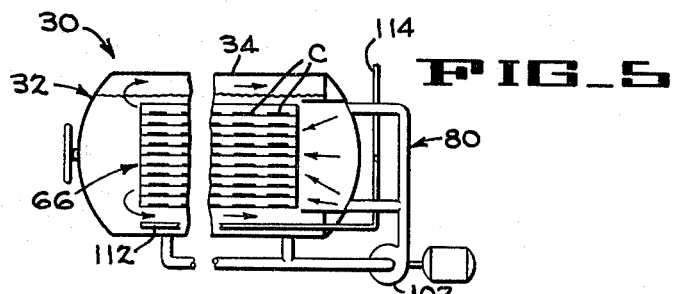
FIG_5
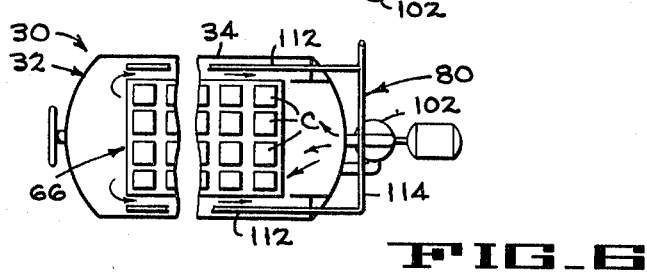
FIG_6
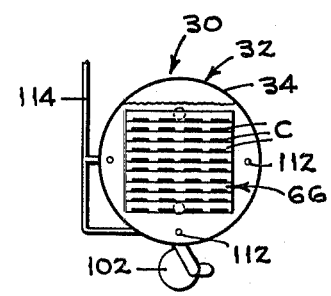
FIG_7

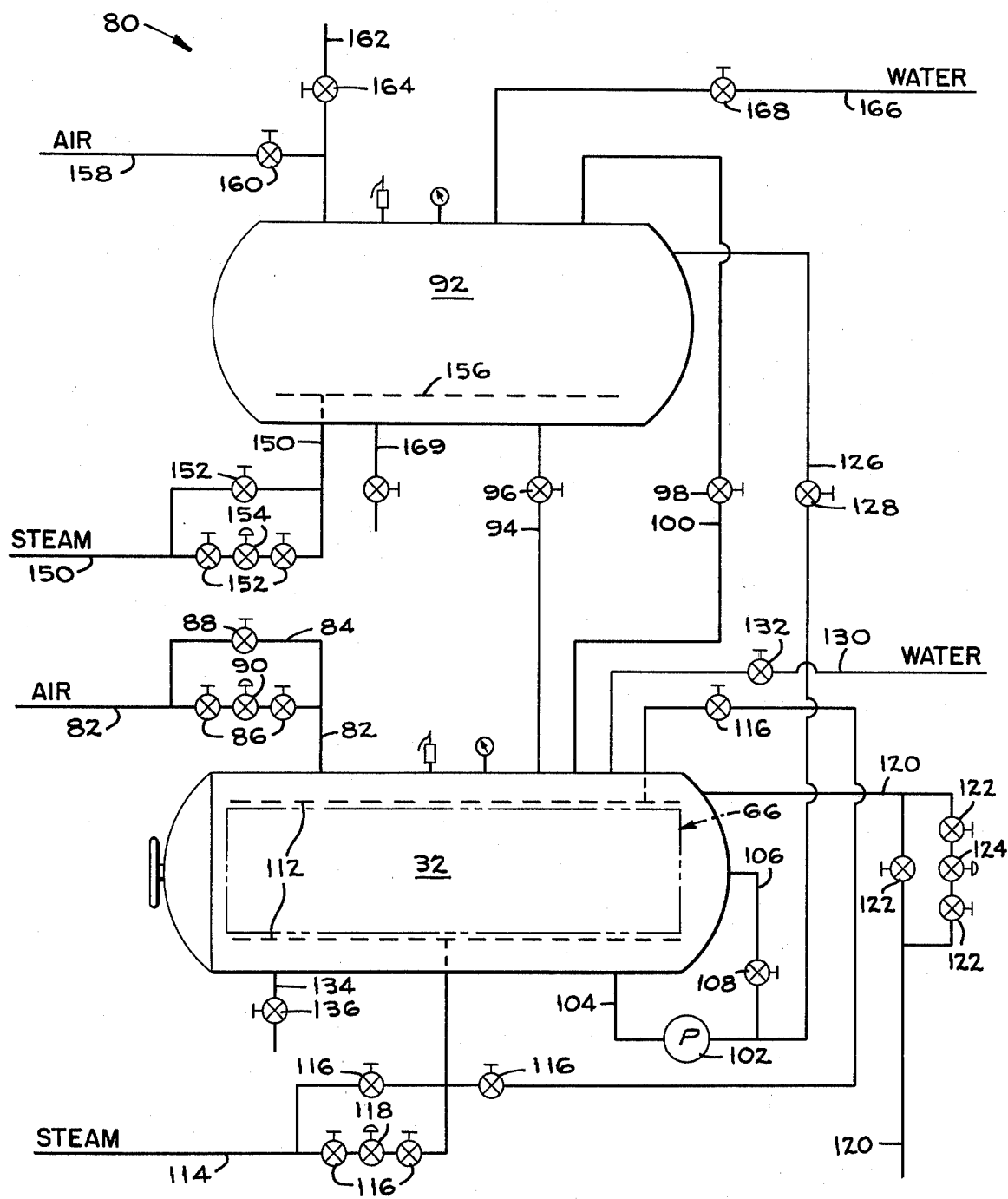
FIG_4

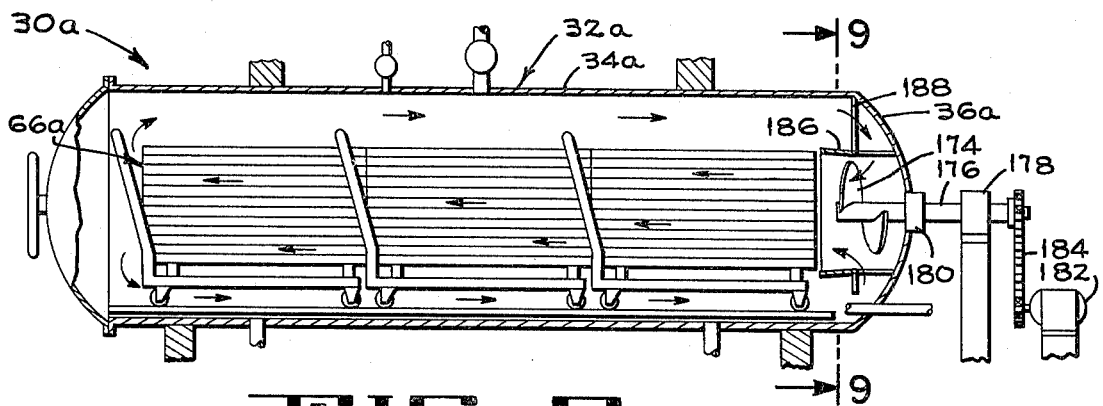
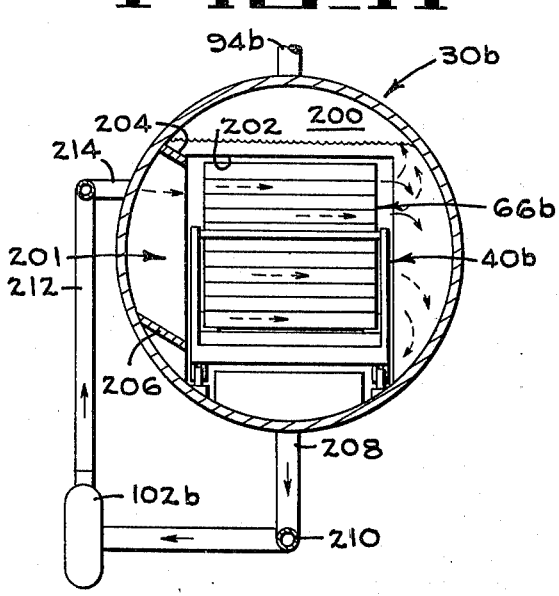
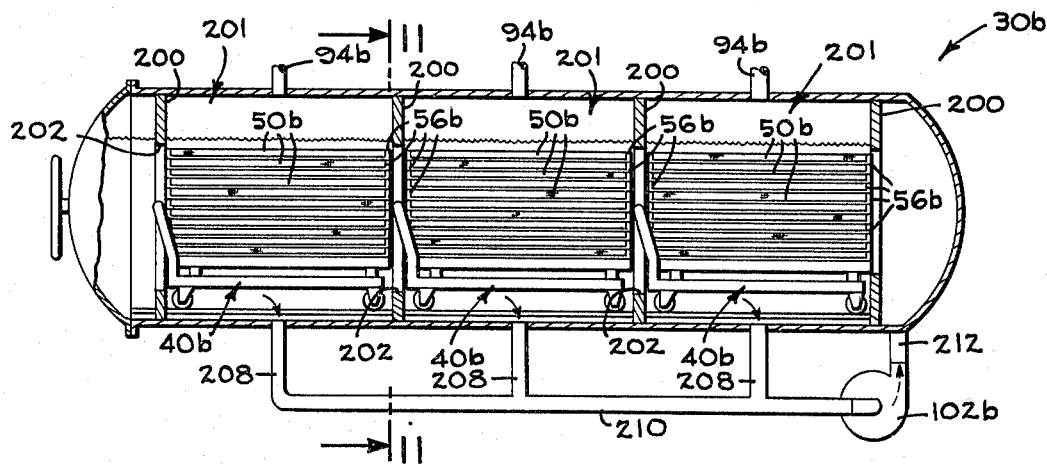

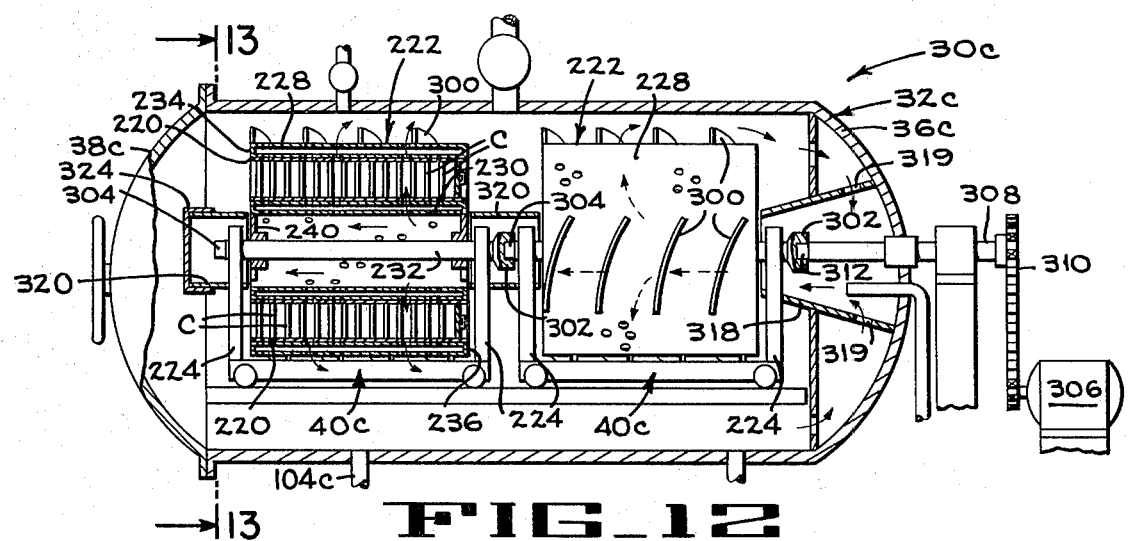
FIG_12
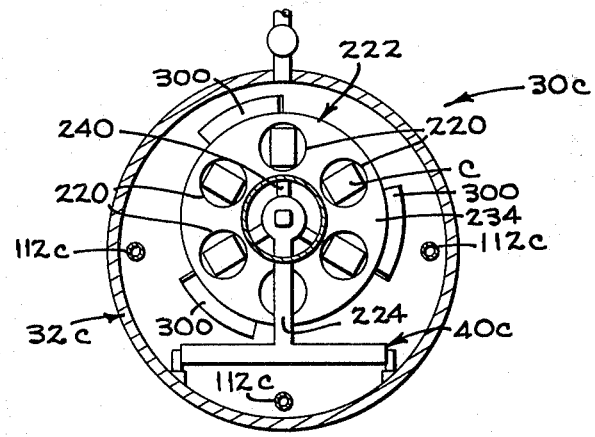
FIG_13
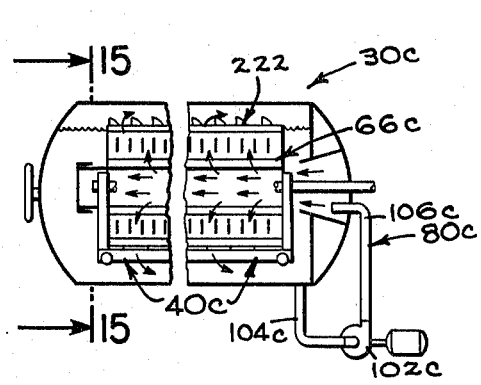
FIG_14
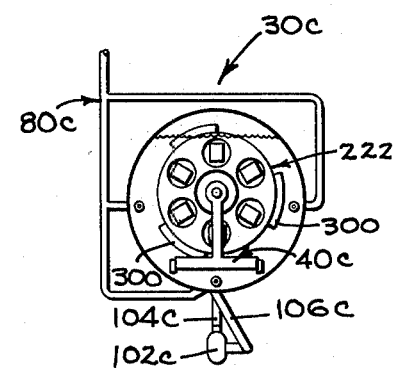
FIG_15

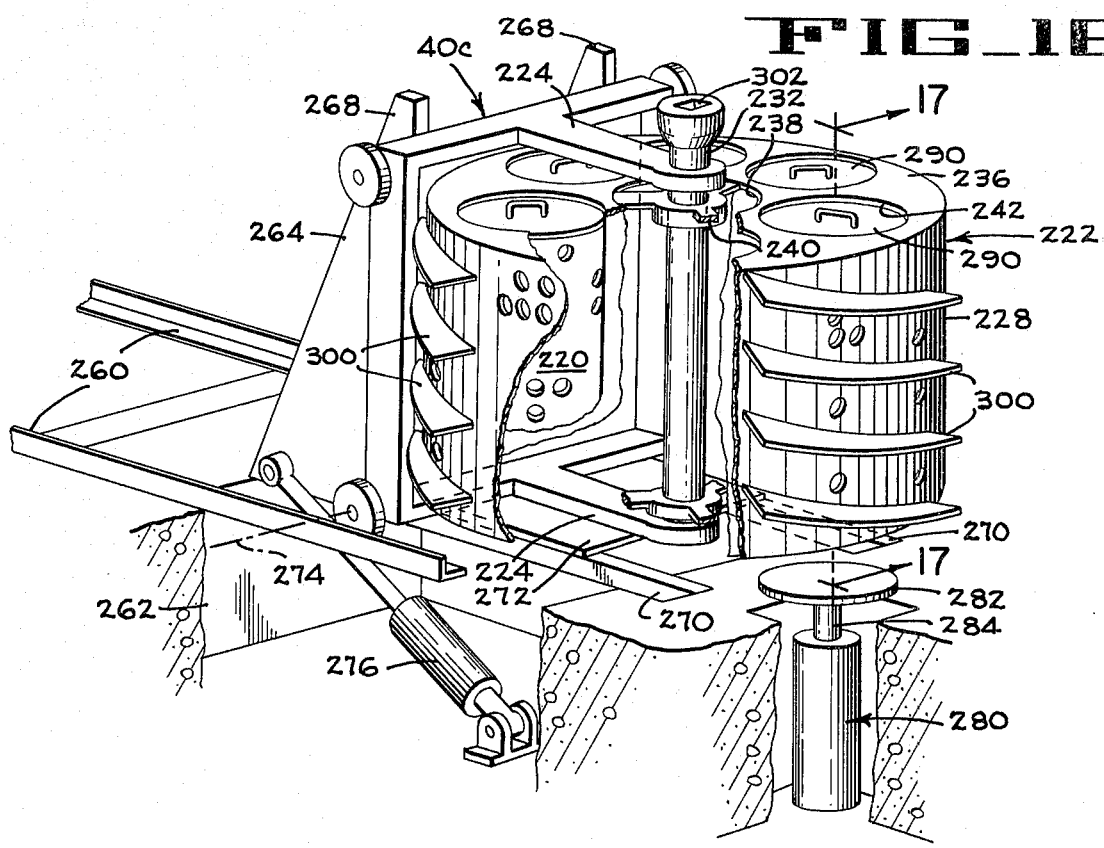
FIG_16
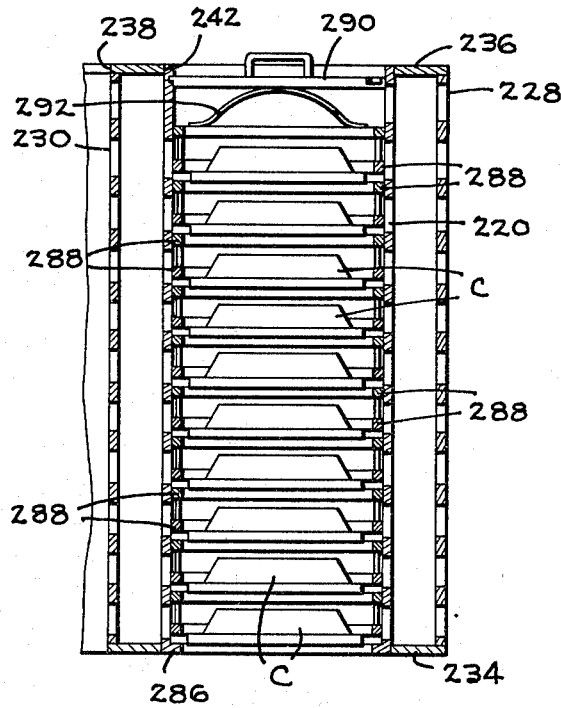
FIG_17
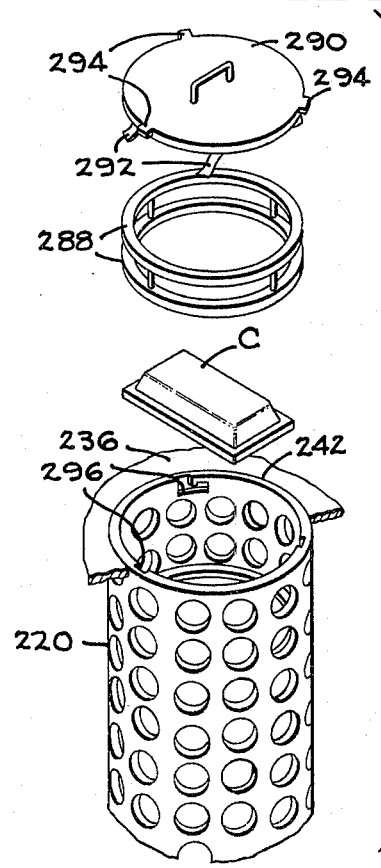
FIG_18

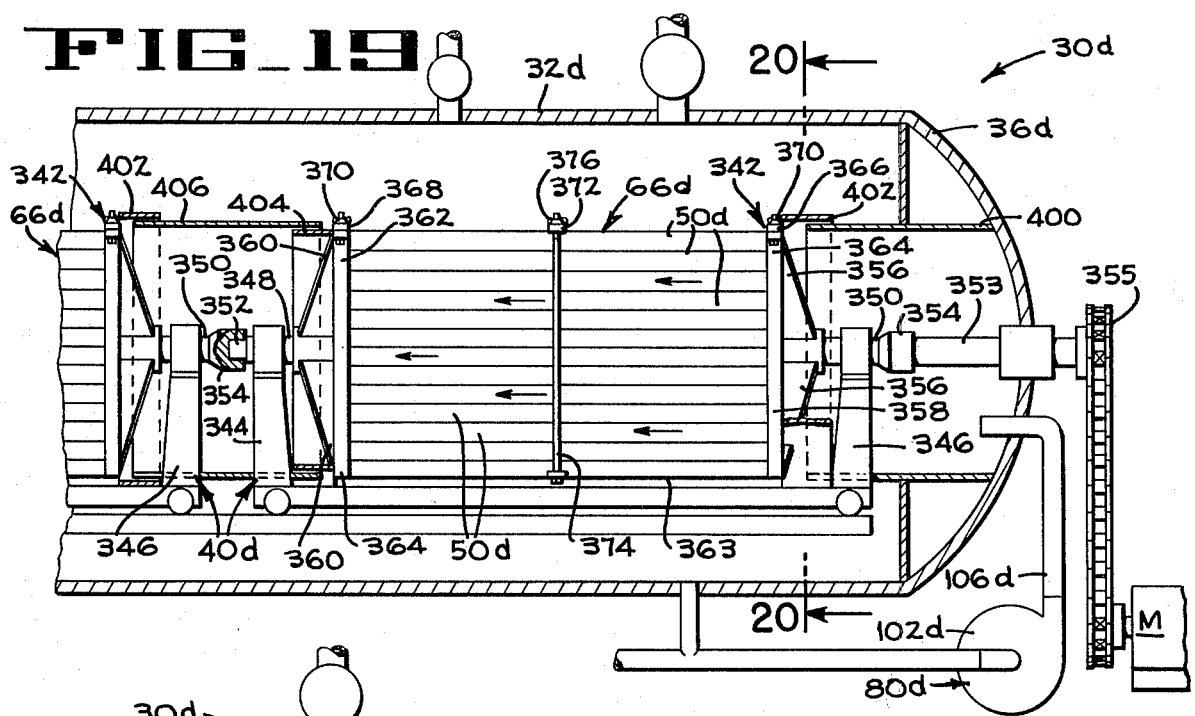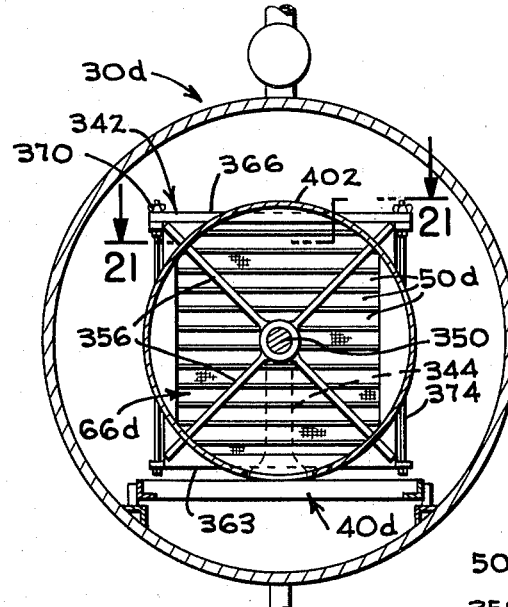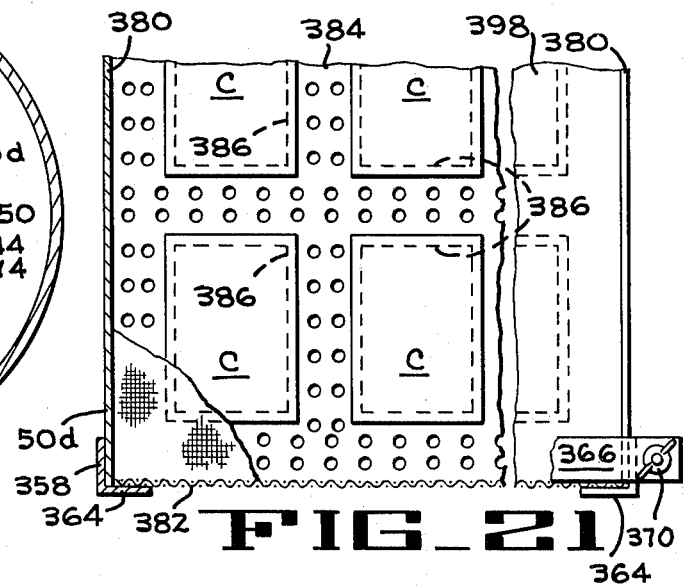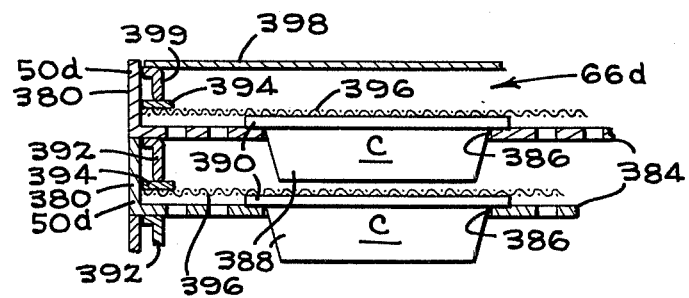

RETORT SYSTEM

BACKGROUND OF THE INVENTION

1. Field of the Invention

This invention pertains to retort systems for generally flat containers, and more particularly relates to a system for heating or cooling filled, thin walled generally flat containers having fast heat penetration rates for more evenly and efficiently heating all containers in a batch of containers to assure a uniformly cooked product.

2. Description of the Prior Art

Agitating and non-agitating batch type high pressure cookers and coolers are well known in the art. In general these retort systems receive batches of containers, such as cylindrical cans or jars, which are first heated by hot water until sterilized and are thereafter cooled by cold water. In order to prevent damage to the containers where the pressure within the containers exceeds the pressure externally of the containers, an overriding air pressure is usually applied over the water in these prior art devices. Also, if the water within the pressure vessel or retort is circulated, it is usually merely cascaded down upon the flat upper ends of the upper containers, or is moved horizontally against the rounded surfaces of the outer upstream containers, with little regard to whether or not the lower tiers of containers and the containers near the middle of the batch of containers receive the same amount of heat as the upper or outer containers.

The U.S. Pat. No. Davis 2,629,312 issued Feb. 24, 1953, is somewhat pertinent to the present invention in that the patentee discloses a pressure cooker or retort system arranged to receive a plurality of containers in retort baskets on an elongated reel. The baskets are moved into the cooker or retort on wheels formed integrally with each basket. The baskets are also rotated during processing in response to rotating the elongated reel. In the Davis apparatus steam, not hot water, is used as the heating medium.

Prior U.S. Pat. No. 3,480,451 to Hardison, issued Nov. 25, 1969, also discloses a retort having trackways for receiving cases of bottled goods, and drive means for rotating the entire retort during processing.

Prior U.S. Pat. No. 3,744,402 to Piegza et al, issued July 19, 1973, discloses a retort having a plurality of article supporting baskets mounted for rotation with a rotatable fluid distributing shaft assembly. One end wall of the retort, and the baskets, are moved along tracks to expose the baskets for loading and unloading.

Prior U.S. Pat. No. 3,776,257 to Piegza, issued Dec. 4, 1973 discloses a high pressure retort with flat walls which separate an article and liquid filled treatment chamber from the outer curved areas of the retort thereby reducing the amount of liquid processing medium required. A gas pressure is applied to the external surfaces of the flat walls to prevent pressure induced bowing of the flat walls.

An apparently unpatented retort system is also known wherein batches of cylindrical cans standing on end are positioned within a pressure vessel between vertical side walls. The cans are cooked by using a fan to draw hot air from an inlet end between the side walls past the cans and thereafter returning the hot air to the inlet end externally of the side walls. After cooking, the cans are cooled by directing sprays of cold water downwardly onto the cans.

Although broadly pertinent to the present invention it will be apparent that none of the above patents disclose controlled circulation of the processing liquids parallel to the walls of flat containers as in the present invention.

SUMMARY OF THE INVENTION

The control of the circulation of the processing liquids becomes important when cooking or cooling substantially flat convenience food containers having thin walls with fast heat penetrations rates. The convenience food containers adapted to be processed with the retort system of the present invention are preferably laminated aluminum foil pouches, laminated aluminum foil trays or cups or similar shelf-stable containers which will store foods for long periods after sterilization without requiring refrigeration. Because of the fast heat penetration rate of these thin walled containers, effective control over the heat treatment medium is required if a food product of high quality is to be produced.

In order to obtain the most palatable product possible within the containers, the cooking time and temperature should be closely controlled and should not vary to any appreciable extend among the plurality of containers in a batch being cooked. It is also desirable for best palatability of certain products, such as meat, that the product be inverted from time to time to baste the meat and to provide a uniform cooking on all sides of the meat. Since the containers used in the retort system of the present invention have a very fast heat penetration rate, the heat is withdrawn from the heating liquid and is transmitted to the food product at a faster rate than with conventional food containers. Thus, hot spots and cold spots cannot be tolerated in the heating liquid if a high quality food product is to be produced.

The retort system of the present invention includes a pressure vessel having one or more tunnels formed therein for accommodating batches of flat containers. A liquid heat treatment medium, preferably water is utilized which may include a cooking medium and a cooling medium. The cooking medium is raised to a cooking/sterilizing temperature externally of the tunnel and is thereafter directed into the inlet end of the tunnel for movement past the containers and out the discharge end of the tunnel for recirculation and reheating externally of the tunnel. In this way the temperature of the heating medium when it contacts the containers will be uniform and will not include hot spots or cold spots which might be injurious to the product.

The containers are oriented in the tunnel with their flat sides parallel to the direction of movement of the heating liquid for more uniform heat transfer to the containers. The rate of flow of liquid is sufficient to permit only about a one degree drop in temperature of the heating medium from the input to the output end of the tunnel.

In the preferred embodiment of the invention, the containers are placed in processing trays supported by a cart for movement into and out of the retort. The cart includes an imperforate bottom wall and an imperforate roof, which roof is placed on the upper tray to define two walls of the tunnel. The trays nest into each other and have a pair of parallel imperforate side walls which define the other two walls of the tunnel. The remaining walls and the bottom of each processing tray are perforated, and a perforated container hold-down plate is provided in each tray to assure free circulation of the processing liquid about both flat surfaces of each container and for maintaining the containers spaced from each other. The tunnel or tunnels may be disposed longitudinally to transversely of the vessel, and in one embodiment of the invention, the trays are mounted on a reel and the reel is rotated during processing for the purpose of basting the products and otherwise agitating the contents of the containers.

In another embodiment of the invention, individual food containers are loaded into cartridges in a rotatable reel supported on a cart when the reel is vertical. The loading and unloading may be accomplished with the aid of a vertically movable table which projects into each cartridge in turn. After the cart is loaded, it is tilted from a vertical to a horizontal position, moved into the retort, and its reel is coupled to reels of other carts and to a reel drive mechanism which rotates the reels thereby agitating the contents of the containers. In this last mentioned embodiment of the invention a tunnel is defined by radially extending walls of each reel and, the flow of cooking liquid is radially outward.

Although the above discussion has been directed to the cooking medium, it will be understood that the invention likewise covers circulation of a liquid cooling medium through the tunnel to efficiently cool the containers and their contents below the boiling point of water at atmospheric pressure prior to releasing the containers from the retort to the atmosphere.

It is one object of the present invention to provide an improved retort system for processing thin walled, generally flat containers having fast heat penetration rates.

Another object is to provide an improved system for more efficiently directing a heat treatment medium past generally flat containers.

BRIEF DESCRIPTION OF DRAWINGS

FIG. 1 is a diagrammatic elevation of a first embodiment of the retort system of the present invention with the retort being shown in vertical central section with a hot water holding tank therabove.

FIG. 2 is an enlarged vertical section taken along lines 2—2 of FIG. 1 illustrating a flow controlling tunnel partially defined by sidewalls of nesting container supporting trays filled containers therein.

FIG. 3 is an enlarged perspective of two of the container supporting trays of the system of FIG. 2 having containers therein.

FIG. 4 is diagrammatic elevation illustrating the piping and controls for directing steam, air and water into the retort system of FIG. 1.

FIG. 5 is a diagrammatic operational view of the retort system of FIG. 1 in vertical longitudinal section illustrating the direction of circulation of the liquid heat treatment medium through the retort.

FIG. 6 is a diagrammatic operational view similar to FIG. 5 but shown in horizontal section.

FIG. 7 is a diagrammatic operational view similar to FIG. 5 but shown in transverse section and illustrates the tunnel and the containers therein.

FIG. 8 is a vertical central section illustrating a second embodiment of the retort system of the present invention which includes a retort having an internal liquid circulation system.

FIG. 9 is a vertical transverse section taken along lines 9—9 of FIG. 8.

FIG. 10 is a diagrammatic central section of a retort system similar to that shown in FIG. 1 but illustrating a third embodiment of the invention having the water circulation tunnels extending transversely of the retort.

FIG. 11 is an enlarged transverse section taken along lines 11—11 of FIG. 10.

FIG. 12 is a diagrammatic central section of a retort system similar to that shown in FIG. 1 but illustrating a fourth embodiment of the invention, which embodiment includes carts having interconnected driven reels thereon for agitating the contents of the containers.

FIG. 13 is a transverse section taken along lines 13—13 of FIG. 12.

FIG. 14 is an operational view in horizontal central section illustrating the flow pattern of the liquid heat treatment medium in the retort system of FIG. 12.

FIG. 15 is an operational view in transverse section taken along lines 15—15 of FIG. 14.

FIG. 16 is a perspective of a system for loading containers into and unloading containers from the agitating reels of the retort system shown in FIG. 12, the view illustrating a cart tilted into a vertical position.

FIG. 17 is an enlarged central section taken along lines 17—17 of FIG. 16 and illustrating one of the cartridges of the agitating reel shown in FIG. 16 after it has been filled with containers.

FIG. 18 is an exploded view of the cartridge and cover shown in FIG. 17.

FIG. 19 is a vertical central section of the drive end of a fifth embodiment of the invention illustrating another type of agitating retort system, said system being adapted to rotate container supporting trays to agitate and baste the food product in the containers.

FIG. 20 is a transverse section taken along lines 20—20 of FIG. 19.

FIG. 21 is an enlarged horizontal section taken along lines 21—21 of FIG. 20 and illustrating a portion of the structure for maintaining the trays in the rotating reel.

FIG. 22 is an enlarged section through a portion of the container supporting trays used in the apparatus disclosed in FIG. 19.

DESCRIPTION OF THE PREFERRED EMBODIMENTS

The retort system 30 (FIGS. 1-7) of the first embodiment of the invention comprises a retort or pressure vessel 32 defined by a cylindrical housing 34 with a front end closure 36 sealing one end and a door 38 on the other end. One or more carts 40 filled with flat containers C (FIG. 3) is moved into or out of the pressure vessel 32 on tracks 42 when the door 38 is open. The containers are cooked/sterilized, and thereafter cooled by liquid heat treatment mediums under superatmospheric conditions when the door 38 is closed. Water is preferred heat treatment liquid and will be referred to in the specification as such although it will be understood that other liquids may be used.

As best shown in FIGS. 1 and 2, each of the carts 40 includes a frame 44 having wheels 46 journaled thereon which ride along the tracks 42. Each cart 40 also includes an upstanding, inverted U-shaped push arm 47, and an imperforate bottom wall 48 upon which a plurality of nesting container supporting trays 50 are carried. Each tray 50 (FIG. 3) includes a perforated bottom wall 52 a pair of perforated end walls 54, and a pair of substantially parallel imperforate side walls 56. The containers C are preferably thin walled generally flat pouches CP, convenience food trays CT, or the like. The containers C preferably have aluminum or laminated aluminum walls having fast heat penetration rates and are placed in the associated trays 50 with their flat walls supported on the bottom tray wall 52. The containers are held in place and from flotation in each tray 50 by a perforated hold-down plate 58 of expanded metal or the like, which plate is held in place by the side walls 56 of the next upper tray 50. An imperforate plate or top wall 62 is placed on the uppermost tray. The imperforate bottom wall 48, nesting side walls 56 of the trays, and the top wall 62 cooperate to define a processing tunnel 66 (FIGS. 5–6) for guiding the processing liquid past the containers C in a direction parallel to the substantially flat side walls of the containers.

FIGS. 1 and 4 diagrammatically illustrate a water, steam, and air circulation system 80 for first cooking and thereafter cooling the flat containers C. After the pressure vessel 32 has been loaded with one or more carts of trays full of flat containers, and the door 38 has been closed and sealed, high pressure air is directed into the vessel 32 through air lines 82 and 84 having valves 86 and 88 and a pressure regulator 90 therein. The pressure within the vessel is raised to about 20 psi gauge before hot water at about 250° F. is released into the vessel from a hot water holding tank 92 thereby assuring that the pressure inside the containers, will not exceed the pressure acting on the external surfaces of the containers enough to cause rupture of the containers. During this vessel filling time, which is known in the art as come-up time and requires about 5 minutes, hot water flows from the holding tank 92 through a conduit 94 having a holding tank valve 96 therein and into the vessel 32 to fill the vessel with water to a level above the top of the tunnel 66. During come-up time, heat from the water raises the temperature of the containers, carts, and the walls of the vessel 32 to a temperature near the processing temperature. A valve 98 in a pressure equalizing conduit 100 is open during the come-up time to equalize the pressure in the vessel 32 and tank 92.

The equalizing valve 98 and the holding tank valve 96 are then closed and a pump 102 is started to draw water through suction conduit 104 from the vessel 32 at a point outside of the tunnel 66. The pump 102 directs the water through high pressure conduit 106, and open valves 108 into the inlet end of the processing tunnel 66 for flow therethrough in the direction indicated by arrows in FIG. 1. During cooking/sterilizing of the containers, the water, of course, releases heat to the containers C and must be reheated. In order to maintain the hot water at the desired processing temperature and yet not subject any of the containers to hot spots, steam is directed into the vessel 32 through perforated steam pipes 112 disposed externally of the tunnel 66 as best shown in FIGS. 6 and 7. Steam is supplied to the perforated steam pipes 112 from a source of steam (not shown) through conduit 114 (FIG. 4) having steam valves 116 and a temperature regulator 118 therein. Overflow water is discharged from the vessel 32 through conduit 120 having valves 122 and a pressure regulator 124 therein.

After the cooking cycle has been completed, the valve 108 is closed, the hot water is pumped from the vessel 32 into the holding tank 92 through conduit 126 having valve 128 therein. During this time, pressure equalizing valve 98 is open and air pressure is maintained at about 20 psi in the tank 92 and in the vessel 32 to prevent rupture of the hot containers.

After substantially all the hot water is transferred from the vessel 32 to the holding tank 92, the valve 128 is closed and cooling water is added to the pressure vessel 32 through conduit 130 and open valve 132. After the vessel has been filled with cooling water, the pump 102 circulates the water through the tunnel 66 to cool the containers. During this time some of the coolant may be drained from the vessel through drain conduit 134 and open valve 136 and additional cold water may be added through conduit 130 if desired. During cooling, the air pressure from conduit 82 is gradually reduced until the containers are cooled sufficiently to allow the vessel to be reduced to atmospheric pressure. All the water is then drained from the vessel 32, through conduit 134, the door 38 is opened, and the carts of processed containers are removed from the vessel.

The water stored in the tank 92 is heated to about 250° F by steam directed into the tank 92 through conduit 150, valves 152, temperature regulator 154 and a perforated steam pipe 156. The tank 92 is also provided with a high pressure air conduit 158 having a valve 160 therein, and a vent 162 having a valve 164 therein. Makeup water is supplied to the tank 92 through conduit 166 having a valve 168 therein, and the tank 92 may be drained by valved conduit 169.

As mentioned above, the substantially flat containers C being processed by the retort system 30 of the present invention are thin walled containers, such as aluminum pouches or trays, having fast heat penetration rates. In accordance with the present invention the processing time is reduced by positioning the containers so that the heat treatment liquid flows parallel to and past both flat sides of each container thereby subjecting large flat areas of each container to a heat treatment liquid flowing therepast without creating voids on the downstream side of the container as would occur if the flow was normal to the flat sides of the container. In order to limit the temperature change of the heating liquid in the tunnel to about 1° F from the inlet to the outlet of the tunnel, it has been determined that the rate of flow of the heating liquid through the tunnel should be such that the heated liquid entering the tunnel will leave the tunnel in about 30 seconds. Thus, if the tunnel 66 is 6 feet long, the heat treatment liquid should be flowing at about 12 feet per minute; and if the tunnel is 12 feet long the heat treatment liquid should flow at about 24 feet per minute for best results. It will be understood that when two or more carts are positioned in end to end relation as indicated in FIG. 1 that the length of the tunnel will be the distance between the inlet end of the first cart and the discharge end of the last cart.

A second embodiment 30a of the retort system is illustrated in FIGS. 8 and 9 and is identical to the first embodiment 30 of the invention except for the system for circulating water through the tunnel 66a formed in the pressure vessel 32a.

As diagrammatically illustrated in FIG. 8, the water is circulated by a helix 174 secured to a shaft 176 journaled in a bearing 178 and a stuffing box 180 secured to the end closure 36a of the vessel 32a. The shaft 176 is driven by a motor 182 and a chain drive 184 to circulate the water at the proper rate and in the direction indicated by the arrows in FIG. 8. As best shown in FIG. 9, an annulus 186 is secured to the cylindrical wall 34a of the vessel by radial legs 188 and serves to guide the heat treatment liquid pumped forwardly by the helix into the tunnel 66a while receiving the reheated liquid externally of the tunnel through openings in the rear portion of the annulus.

A third embodiment of the retort system 30b of the present invention is illustrated in FIGS. 10 and 11 and is substantially the same as the first described embodiment 30 of the invention except that the solid side walls 56b of the nesting trays 50b on each cart 40b are oriented transversely rather than longitudinally of the pressure vessel 32b. Thus, the trays 50b in each cart, and cooperating transverse baffles 200, define their own transverse processing sections 201. The baffles 200 each include a generally rectangular opening 202 for permitting several short handled carts 40b to be positioned in the pressure vessel 32b as illustrated in FIG. 10. In addition to the baffles 200, longitudinally extending upper baffles 204 (FIG. 11) and lower baffles 206 in each processing section 201 aid in directing the relatively high pressure heat treatment liquid into the associated tunnel 66b in each transverse processing section 201.

The heat treatment liquid is circulated by a pump 102b which receives the liquid from each section 201 of the vessel 32b below each cart 40b by separate suction pipes 208 and a main suction conduit 210. The pump 102b directs the relatively high pressure liquid through a main supply pipe 212 through individual pipes 214 (only one being shown in FIG. 11) into each processing section 201. Also, each processing section 201 has its own valved conduit 94b for receiving hot liquid from a holding tank (not shown) which is similar to the holding tank 92 of the first described embodiment 30 of the invention. In other respects the water, steam and air recirculation system 80b used with the third embodiment 30b of the retort system of the invention operates in a manner substantially the same as that of the first described embodiment of the invention.

The three above described embodiments of the retort system of the present invention illustrates different forms of non-agitating retort systems. If the flat containers C are thick, for example in excess of about 1¼ inches or if the containers are filled or partially filled with a product such as meat that should be basted, it has been determined that such containers should be agitated during cooking for best results.

FIGS. 12–18 illustrate a fourth embodiment of the invention in the form of an agitating retort system 30c including a system for loading containers C into and unloading containers C from perforated cartridges 220 (FIGS. 16–18) formed in one or more reels 222 journaled for rotation in upstanding arms 224 of associated carts 40c. Parts of the fourth embodiment 30c of the retort system which are similar to those of the first embodiment of the invention will not be described in detail but will be assigned the same numerals followed by the letter "c".

As diagrammatically illustrated in FIG. 12, two carts 40c are in their normal horizontal positions within a pressure vessel 32c with the door 38c being closed.

Each cart 40c supports a reel 222, and each reel 222 includes an outer cylindrical wall 228 (FIGS. 12, 16 and 17) and an inner cylindrical wall 230 both of which are perforated throughout to allow the heat treatment liquid to flow therethrough as indicated by the arrows in FIG. 12. The cylindrical walls 228 and 230 are secured to a shaft 232 by annular end walls 234 and 236 having central openings 238 (FIG. 16) therein. The end walls are connected to the shaft 232 by radial legs 240 with the inner and outer cylindrical walls 230 and 228 being concentric with the shaft 232. The end walls 234 and 236 also have a plurality of equally spaced openings 242 therein to which the aforementioned perforated cartridges 220 are rigidly secured as best shown in FIG. 17.

Although the drawings do not show all of the holes in the cylindrical walls 228, 230, and in the cylindrical walls of the cartridges 220, it will be understood that each of these walls are fully perforated.

As indicated in FIG. 16, 17 and 18, the containers C are manually loaded into and unloaded from the cartridges 220 when the normally horizontal cartridges are positioned vertically. In this regard, during the container loading and unloading operation each cart 40c is moved along tracks 260 over a pit 262 and onto a tilting mechanism 264. The tilting mechanism 264 is not critical to the invention but is illustrated and described to give a better understanding of how the containers C are loaded into and unloaded from the cartridges.

The tilting mechanism 264 includes arms 268 that are rigidly secured to forks 270 projecting at right angles therefrom and interconnected by a support beam 272. The arms 268 are journaled in bearings (not shown) and are pivoted about an axis 274 from a normally horizontal position within the pit 262 to the illustrated upstanding position by a hydraulic cylinder 276. As indicated in FIG. 16, the arms 268 engage the normally horizontal frame 44c of the cart 40c, and cross beam 272 engages one of the upstanding cart arms 224 to support the cart when it is pivoted into the loading/unloading position illustrated in FIG. 16. When in the loading/unloading position, each cartridge 220 may be easily indexed in turn over an operator controlled loading/unloading ram 280 having a container supporting plate 282 on its piston rod 284 for gradual movement upwardly into the cartridge during unloading, and gradual movement downwardly during loading.

As indicated in FIG. 17, each cartridge 220 includes a container supporting annulus 286 on its lower end which supports the corners of the lowermost container C. Normally the shape and strength of the lowermost container C is sufficient to close the lower end of the cartridge 220 sufficiently to control the flow of water substantially radially there past. However, if the containers are too flexible or too small to adequately control the flow of liquid, it will be understood that it is within the scope of the invention to insert an imperforate disc or the like, (not shown) upon the annulus 286 to close the lower end of the cartridge. Spacer rings 288 (FIGS. 17 and 18) and containers C are thereafter alternately lowered into the cartridge 220 with the aid of the ram 280 until the cartridge is fully loaded. A cap 290 having leaf springs 292 thereon which engage the uppermost spacer ring 288 is then inserted into the cartridge 220. The cap 290 is locked in place by ears 294 which are received in locking slots 296 formed in the inner surface of the cartridge 220.

Helical vanes 300 are secured to the outer surfaces of each reel 222 to aid in circulating the treatment liquid during processing as indicated by the arrows in FIG. 12. During processing, the reels 222 are interconnected by a non-circular socket 302 on one end of each shaft 232 and a mating non-circular drive member 304 formed on the other end of each shaft. The reels 222 are driven in the range of about 2–5 revolutions per minute by a motor 306 that is connected to a drive shaft 308 by a chain drive 310. The drive shaft 308 is journaled for rotation and projects through the end closure 36c of the pressure vessel 32c. The drive shaft 308 includes a noncircular drive member 312 which drivingly engages the adjacent socket 302 to drive the reels.

It will be apparent from FIGS. 12 and 14 that the heat treatment liquid is directed under pressure axially into the inner perforated cylindrical wall 230 of each reel 222 and flows radially outward through the inner wall, radially through each cartridge 220 past the flat side walls of the container C, and out through the perforated outer cylindrical wall 228. Thus, the processing tunnel 66c of each reel is defined by the annular end walls 234 and 236, the previously referred to end containers in each cartridge 220 (or cartridge closure disc, not shown) and the cartridge closing caps 290.

A water, steam, and air circulation system 80c is only partially illustrated in FIGS. 12-15 but is substantially the same as the system 80 (FIG. 4) of the first embodiment of invention and accordingly will not be described in detail. It will be sufficient to note that the pump 102c (FIGS. 14 and 15) directs the high pressure liquid into the pressure vessel 32c through conduit 106c. The relatively high pressure liquid is guided into the perforated inner cylindrical wall 230 of the adjacent reel 222 by a frusto-conical baffle 318 having recirculating openings 319 therein. Tunnel sections in the form of rings 320 are secured to the downstream arms 224 of the associated carts 40c and have slots in their lower portions to receive the upstream arms 224 of the next adjacent downstream cart 40c as illustrated in FIG. 12. The ring 320 of the last cart is closed by a cap 324 to prevent flow of the heat treatment liquid therethrough thereby assuring that the water will flow radially through the radial processing tunnel 66c defined in each reel 222. The vanes 300 aid the suction conduit 104c in moving the cooking liquid past the perforated steam pipes 112c (FIG. 13) for reheating during the cooking cycle and thereafter into the frusto-conical baffle 318 for recirculation through the radial tunnels 66c.

A fifth embodiment 30d of the retort system of the present invention is illustrated in FIGS. 19-22 and is substantially the same as the retort system of the first embodiment except that the carts 40d support trays 50d of containers C on rotatable agitating reels 342.

Since many portions of the retort system 30d are similar to those of the first embodiment of the invention, only the difference will be described in detail, and components of the fifth embodiment of the retort system that are similar to those of the first embodiment will be assigned the same numerals followed by the letter d.

Each cart 40d includes upstanding support members 344 and 346 which journal stub shafts 348 and 250, respectively. A non-circular driving member 352 is formed on one end of the shaft 348 to drivingly engage a socket 354 formed one end of the shaft 350 of the next adjacent cart. A similar socket 354 on the shaft 350 is drivingly engaged by a non-circular driving member (not shown) on a drive shaft 353 journaled in the end closure 36d. The shaft 353 and reels 342 are rotated between about 2 to 5 revolutions per minute by a motor M connected thereto by a chain drive 355. Four radial legs 356 (FIG. 20) are rigidly secured to the other end of the shaft 350 and have a vertically disposed, open rectangular end frame 358 of the reel 342 rigidly secured to their outer ends. Similarly, four radial legs 360 (FIG. 19) are secured to the shaft 348 and have another vertically disposed open rectangular end frame 362 of the reel 342 rigidly secured to their outer ends. An imperforate lower wall 363 of the reel 342 is rigidly secured to the lower edges of the end frames 358 and 362 to define one wall of the processing tunnel 66d and to support a plurality of rectangular nesting trays 50d of containers C thereon.

As indicated in FIG. 21, the vertical portions of the rectangular end frames 358 and 362 are angle members 364 and serve to maintain the corners of the stacks of filled trays 50d in stacked relationship in the reel 342. In order to clamp the trays 50d in the reel, hold down bars 366 and 368 (FIG. 19) extend across the ends of the trays 50d and are secured to the end frames 362 and 358 by wing nuts 370. An intermediate hold down bar 372 extends transversely across the uppermost trays and is clamped between the trays and the lower wall 363 of the reel 342 by elongated bolts 374 and cooperating wing nuts 376.

Although trays disclosed in the first embodiment 30 of the invention may be used in the retort system 30d, a modified form of tray 50d is disclosed in FIGS. 21 and 22. Each tray 50d includes a pair of longitudinally extending, imperforate side walls 380, perforated transverse end walls 382 and a perforated floor 384. A plurality of large openings 386 are formed in the floor for receiving the bodies 388 of associated containers C while the covers and flanges 390 of the containers remain supported on the upper surface of the floor 384 (see FIG. 22). The containers C are firmly held in place by longitudinally extending angle bars 392 (FIG. 22) rigidly secured to and projecting downwardly from the lower portion of the floor 384 of the next uppermost tray. The angle bars 392 engage longitudinal straps 394 on the edges of perforated hold down plates 396 resting on the covers of the containers as clearly illustrated in FIG. 22. An imperforate upper wall 398 having downwardly projecting spacer flanges 399 is clamped in the upper tray 50d in each cart 40d by the previously described bars 366,368 and 372 (FIG. 19). Thus, the imperforate upper wall 398, the imperforate lower wall 363 of the reel 342, and the imperforate nesting side walls 380 of the trays 50d cooperate to define a processing tunnel 66d in each cart.

As indicated in FIG. 19, the pump 102d of the water, steam and air circulation system 80d directs the heat treatment liquid through conduit 106d into the pressure vessel 32d. The high pressure processing liquid is guided by a stationary annulus 400 into a larger diameter rotary annulus 402 connected to the rectangular end frame 358 of a reel 342. It will be understood that the lower portion of the stationary annulus 400 is slotted to receive the reel support member 346 of the end cart 40d. The heat treatment liquid then flows through the previously described tunnel 66d in the upstream cart 40d in a direction parallel to the flat walls of the containers as indicated by arrows in the tunnel in FIG. 19. Thereafter, the heat treatment liquid flows through a small diameter rotary annulus 404 secured to the rectangular frame 362 of the end reel 342 and into a larger diameter stationary annulus 406 secured to the reel support member 344 of the end or upstream cart 40d. The heat treatment liquid then flows into the rotating annulus 402 of the next adjacent downstream cart for movement into the processing tunnel 66d of that cart. The flow continues as above described for each cart in turn and is eventually discharged through the stationary annulus 406 of the last cart being processed. The discharged liquid is then circulated externally of the tunnel (which tunnel includes the tunnel section 66d of all carts and the flow control annuluses therebetween) for reheating (if in the cooking cycle) and recirculation through the elongated processing tunnel 66d. It will be understood that the water, steam and air circulation system 80d and its mode of operation is the same for the fifth embodiment of the invention as described for the first embodiment of the invention and accordingly its description will not be repeated. However, it will be apparent that the fifth embodiment differs from the first embodiment since the motor M rotates the reels 342 within the range of about 2–5 revolutions per minute thereby agitating and basting the product within the containers C during heat treatment.

From the foregoing description it will be apparent that each of the retort systems of the present invention includes a processing tunnel through which a heat treatment liquid flows and within which the thin walled, generally flat containers are supported with their flat walls being parallel to the direction of flow of the liquid. The retort system may either be of the still cook type where the containers are stationary during heat treatment or the agitating type where the containers are rotated during heat treatment.

Although the best modes contemplated for carrying out the present invention have been herein shown and described, it will be apparent that modification and variation may be made without departing from what is regarded to be the subject matter of the invention.

What is claimed is:

1. A retort system for changing the temperature of substantially flat containers having thin flat sidewalls with high heat penetration rates, said system comprising a vessel having an enclosing outer wall and a longitudinal axis, imperforate wall means defining a tunnel disposed within said vessel spaced from at least a portion of said outer wall thereof and having an inlet end and an outlet end for liquid, said imperforate wall means extending between said inlet end and said outlet end to confine the flow of liquid within said tunnel, flow inducing means for moving a heat treatment liquid at a predetermined temperature through said tunnel and past the containers to transfer heat between the containers and the liquid, said flow inducing means thereafter returning the liquid discharged from the tunnel externally of the tunnel between said tunnel and said outer wall of the vessel to the inlet end of the tunnel for recirculation through said tunnel, means for supporting the containers in the tunnel in positions spaced apart in a direction perpendicular to the flow path through the tunnel and so that the flat sidewalls thereof are parallel to the flow direction of the heat treatment liquid, and means for returning the temperature of the liquid to said predetermined temperature as the liquid is moving externally of said tunnel toward said inlet end.

2. An apparatus according to claim 1 wherein the vessel is a pressure vessel and the heat treatment liquid is a heated cooking liquid.

3. An apparatus according to claim 1 wherein said tunnel is disposed parallel to said longitudinal axis of said vessel.

4. An apparatus according to claim 1 wherein said tunnel is disposed normal to said longitudinal axis of said vessel.

5. An apparatus according to claim 1 wherein said flow inducing means is disposed within said vessel.

6. An apparatus according to claim 1 wherein said flow inducing means is disposed externally of said vessel and includes an inlet end and a discharge end, and first conduit means connected between said vessel at a point externally of said tunnel and the inlet end of said flow inducing means, and second conduit means communicating with the inlet end of the tunnel and connected to said discharge end of said flow inducing means.

7. An apparatus according to claim 1 wherein said container supporting means maintain the containers in fixed position in said tunnel during processing.

8. An apparatus according to claim 1 and additionally comprising means for rotating said tunnel and the containers therein about an axis of rotation during processing.

9. An apparatus according to claim 8 wherein said container supporting means maintains the flat side walls of the container normal to said axis of rotation during processing.

10. An apparatus according to claim 8 wherein said container supporting means maintains the flat side walls of the containers parallel to said axis of rotation during processing.

11. A retort system for changing the temperature of substantially flat containers having thin flat sidewalls with high heat penetration rates; said system comprising the combination of a vessel having a longitudinal axis and an enclosing outer wall, imperforate wall means defining a treatment tunnel within said vessel spaced from at least a portion of said outer wall thereof, said imperforate wall means guiding and confining within said tunnel a liquid heat treatment medium which flows from one end of the tunnel to the other end thereof, flow inducing means for moving the heat treatment medium through said tunnel from said one end to the other to rapidly transfer heat between the containers and the heat treatment medium and for thereafter returning the heat treatment medium externally of said tunnel to said one end of said tunnel, means for supporting the containers in the tunnel in positions spaced apart in a direction perpendicular to the flow path through the tunnel and so that the flat sidewalls of the containers are parallel to the flow direction of the heat treatment liquid, and means for returning the heat treatment medium to its initial processing temperature while the heat treatment medium is returning to said one end of said tunnel.

12. An apparatus according to claim 11 wherein the container supporting means is a plurality of nesting trays; each of said trays comprising a pair of spaced imperforate side walls, a pair of perforated end walls normal to the side walls, and a container supporting bottom wall secured to the side walls and end walls, said imperforate side walls when nested with side walls of other trays defining two side walls of said tunnel.

13. An apparatus according to claim 12 wherein said side tunnel walls are disposed parallel to the longitudinal axis of the vessel.

14. An apparatus according to claim 13 wherein said tunnel side walls are disposed normal to the longitudinal axis of said vessel.

15. An apparatus according to claim 12 wherein the trays are stacked upon each other, wherein the lowermost tray in said stack of trays has an imperforate bottom wall therebelow, wherein the uppermost tray in said stack has an imperforate roof thereabove, and wherein said imperforate bottom wall and roof define lower ad upper walls of said tunnel.

16. An apparatus according to claim 11 wherein said container supporting means includes a reel, means mounting said reel for rotation about an axis extending longitudinally of said vessel, a perforated inner cylindrical wall and a perforated outer cylinder wall concentric with said longitudinal axis, said inner cylindrical wall defining an inner liquid flow passage, a pair of spaced radially extending annular walls secured to said cylindrical walls and to said reel mounting means, portions of said radial walls defining walls of said heat treatment tunnel, means for supporting a plurality of containers between said cylindrical walls with their flat sides extending normally of said axis, and means for rotating said reel to agitate said containers, said circulating means being effective to direct the heat treatment medium into said inner liquid flow passage and radially outwardly past said containers for return to said inner flow passage externally of said reel.

17. An apparatus according to claim 16 and additionally comprising means defining helical vane segments on the outer periphery of said outer cylindrical wall for aiding in advancing the heat treatment medium longitudinally of said reel.

18. An apparatus according to claim 11 wherein said vessel is a pressure vessel having a door on one end which may be opened or closed for loading batches of containers into and unloading batches for containers from said vessel.

19. An apparatus according to claim 18 wherein said heat treatment medium is maintained under superatmospheric pressure in said vessel during processing.

20. An apparatus according to claim 19 wherein said flow inducing means for the heat treatment medium includes a pump positioned externally of said vessel.

21. An apparatus according to claim 19 wherein said means for circulating the heat treatment medium includes propelling means defining a plurality of helical segments disposed within said vessel, and means for driving said propelling means.

22. An apparatus according to claim 19 and additionally comprising baffle means within said vessel for dividing said vessel into transverse processing zones with each zone associated with a batch of containers, a plurality of tunnel defining means in said vessel with each tunnel defining means being associated with a selected batch of the containers and being disposed transversely of said longitudinal axis, said flow inducing means being effective to withdraw said heat treatment medium from one end of each of said tunnels and recirculate the liquid for entrance into the other end of each of said tunnel defining means.

23. An apparatus according to claim 11 wherein said heat treatment medium is hot water maintained under superatmospheric pressure.

24. An apparatus according to claim 11 and additionally comprising supply means including means for directing the liquid heating medium into said pressure vessel, means for maintaining the heating medium at a cooking temperature, means for maintaining a predetermined superatmospheric pressure in said vessel during processing, means for draining the heated cooking liquid from said vessel and storing the heated liquid after the product has been cooked while maintaining the containers under superatmospheric pressure, means for directing a cooling fluid into said vessel to cool the product below the boiling point at atmospheric pressure before releasing the pressure in said vessel, and means for draining the cooling fluid from said vessel.

* * * * *

UNITED STATES PATENT AND TRADEMARK OFFICE
CERTIFICATE OF CORRECTION

PATENT NO. : 4,003,302
DATED : January 18, 1977
INVENTOR(S) : Samuel A. Mencacci, Jurgen H. Strasser, and Tom Mansfield It is certified that error appears in the above-identified patent and that said Letters Patent are hereby corrected as shown below:

```
Column 2, line 25, change "extend" to --extent--.
Column 3, line 40, change "therabove" to -- thereabove --.
Column 4, line 53, after "is" insert --the--.
Column 5, line 10, change "(Figs. 5-6)" to --(Figs. 5-7)--.
Column 9, line 49, change "difference" to --differences--.
Column 9, line 53, change "d" to --"d"--.
Column 9, line 55, change "250" to --350--.
Column 12, line 13, change "maintain" to --maintains--.
Column 12, line 59, after "said" insert --tunnel--.
Column 12, line 62, change "claim 13" to --claim 12--.
```

Signed and Sealed this

Tenth Day of January 1978

[SEAL]

Attest:

RUTH C. MASON
*Attesting Officer*

LUTRELLE F. PARKER
*Acting Commissioner of Patents and Trademarks*